US006451770B1

(12) United States Patent
Rijsewijk et al.

(10) Patent No.: US 6,451,770 B1
(45) Date of Patent: Sep. 17, 2002

(54) BOVINE POLYNUCLETIDE VACCINE FOR THE INTRADERMAL ROUTE

(75) Inventors: Franciscus Antonius Maria Rijsewijk, Amsterdam; Remco Siebren Schrijver, Bilthoven; Johannes Theodorus Van Oirschot, Lelystad, all of (NL)

(73) Assignees: Merial, Lyons (FR); ID-DLO Institute of Animal Science and Health, Lelystad (NL)

( * ) Notice: Subject to any disclaimer, the term of this patent is extended or adjusted under 35 U.S.C. 154(b) by 0 days.

(21) Appl. No.: 09/232,469

(22) Filed: Jan. 15, 1999

Related U.S. Application Data

(63) Continuation-in-part of application No. PCT/FR97/01322, filed on Jul. 16, 1997.

(30) Foreign Application Priority Data

Jul. 19, 1996 (FR) .............................................. 96/09402

(51) Int. Cl.⁷ ...................... A61K 48/00; C12N 15/74; A61M 5/30
(52) U.S. Cl. ...................... 514/44; 435/320.1; 604/70
(58) Field of Search ...................... 514/44; 435/320.1; 604/70

(56) References Cited

FOREIGN PATENT DOCUMENTS

| FR | 2348709 A | 11/1977 |
|---|---|---|
| WO | WO 92/01471 | 2/1992 |
| WO | WO 95/20660 | 8/1995 |

OTHER PUBLICATIONS

Verma et al. (1997) Nature, vol. 389, 239–242.*
Bohm et al. (1996) J. Immunol. Methods, vol. 193, 29–40.*
Orkin et al. (1995) "Report and Recommendations of the Panel to Assess the NIH . . . ".*
Marshall et al. (1995) Science, vol. 269, 1050–1055.*
E. Raz, et al., "Intradermal Gene Immunization: The Possible Role of DNA Uptake In The Induction of Cellular Immunity To Viruses", Proceedings of The National Academy of Sciences of USA, vol. 91, No. 20 (1994) pp. 9519–9523.
H.L. Vahlsing, et al., "Immunization With Plasmid DNA Using a Pneumatic Gun", Journal of Immunological Methods, vol. 175 (1994) pp. 11–22.

* cited by examiner

*Primary Examiner*—Scott D. Priebe
*Assistant Examiner*—Anne Marie S. Beckerley
(74) *Attorney, Agent, or Firm*—Frommer Lawrence & Haug, LLP; William S. Frommer; Thomas J. Kowalski

(57) ABSTRACT

Disclosed and claimed is the use of a liquid jet intradermal administration apparatus that administers a composition: without a needle; and in the epidermis, dermis and/or hypodermis, such as a Pigjet apparatus, for administering bovine vaccines or immunogenic compositions, especially bovine plasmid vaccines or immunogenic compositions. Accordingly, the invention involves bovine immunogenic or vaccine compositions in such an apparatus, and methods for vaccinating bovines or for inducing an immunogenic response in bovines employing such an apparatus, as well as the apparatus containing bovine immunogenic or vaccine compositions.

80 Claims, 2 Drawing Sheets

FIG. 2

BOVINE POLYNUCLETIDE VACCINE FOR THE INTRADERMAL ROUTE

Figure 1:
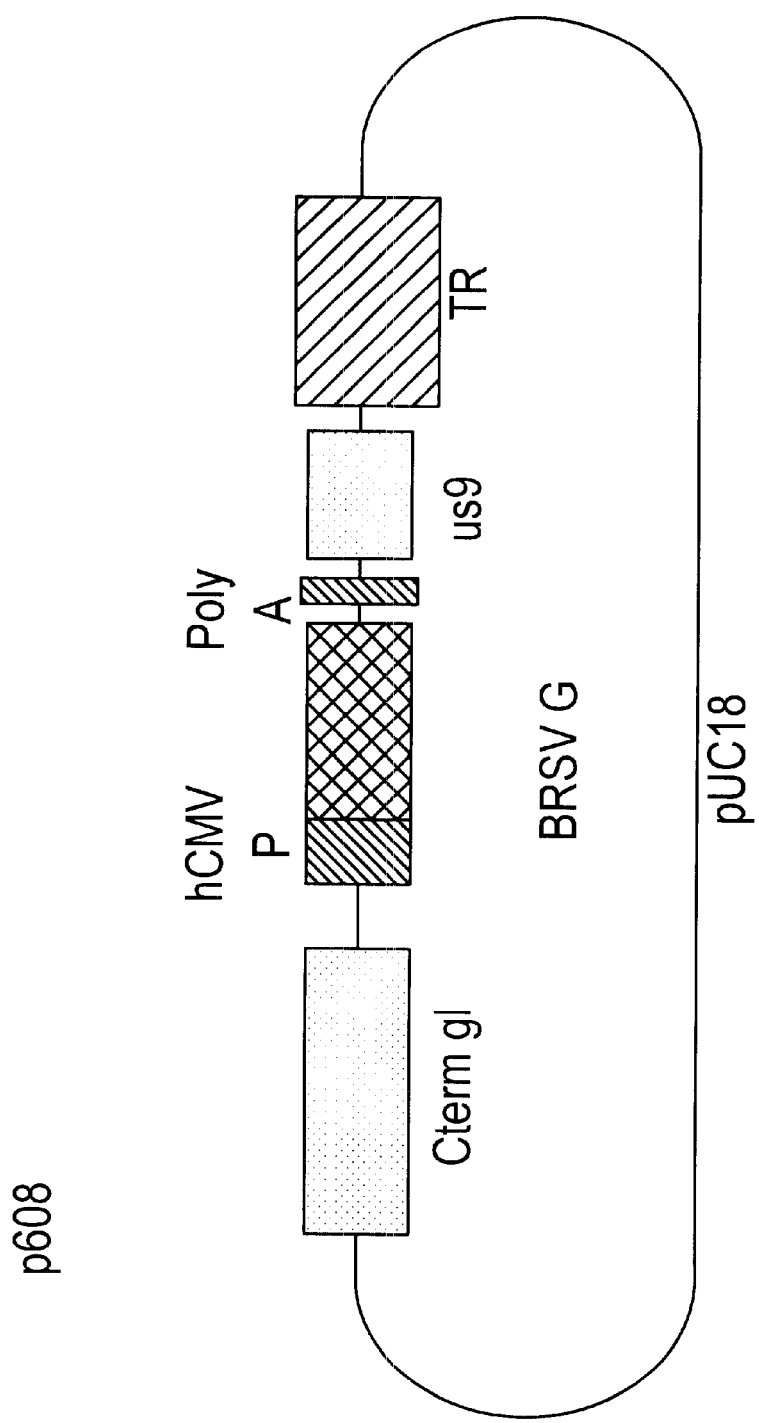

This is a continuation-in-part of copending International Application PCT/FR97/01322 having an international filing date of Jul. 16, 1997, and designating the U.S. and claiming priority from French application Serial No. 96/09402, filed Jul. 16, 1996. All of the above-mentioned applications, as well as documents cited herein and documents referenced or cited in documents cited herein, are hereby incorporated herein by reference. Vectors of vaccines or immunological compositions of documents cited herein or documents referenced in documents cited herein or portions of such vectors (e.g., one or more or all of regulatory sequences such as DNA for promoter, leader for secretion, terminator), may to the extent practicable with respect to the preferred host and administration route of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors; see also PCT/IB97/01040, filed Jul. 28, 1997 and designating the U.S., incorporated herein by reference.

The present invention relates to an improvement made to the vaccination of bovines.

Immunization and vaccination by direct administration of nucleotide sequences encoding an immunogenic protein (called DNA or polynucleotide vaccination) has been described in Patent Application WO-A-90 11092. The protein encoded by the inserted nucleotide sequence is capable of being expressed in the cells and of bringing about the development of an immune response. (See also U.S. Pat. Nos. 5,846,946, 5,620,896, 5,643,578, 5,580,589, 5,589,466, 5,693,622, and 5,703,055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8):801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.). This application envisages the use of naked DNA as well as of DNA contained in liposomes. Preferably, the DNA is introduced into the muscle. The DNA could also be introduced into the skin, into certain organs or into the blood, making it possible for the injection to be carried out in different ways such as by the intradermal route, the transcutaneous route, the intravenous route and the like.

The studies which followed the first descriptions of this technique have demonstrated the benefit of using either the intramuscular route for injecting DNA, or the so-called "gene gun" method which consists in propelling metallic microparticles, such as gold microparticles coated with DNA, directly into the superficial cell layer of the skin.

J. B. ULMER et al., Science, Volume 259, 19 March 1993, 1745–1749; G. J. M. COX et al., J. of Virology, Volume 67, No. 9, September 1993, 5664–5667 and Z. Q. XIANG in Virology 199, 132–140 (1994), have described DNA vaccination trials using the intramuscular route.

It has also been widely demonstrated that the intramuscular route gives superior results to the intradermal route but that, in the final analysis, the most promising route is the use of "gene gun" because, with this technique, the administered doses are much less than the doses required by the intramuscular route. Reference may be made to F. FYNAN et al., in P.N.A.S. USA Volume 90, 11478–11482, December 1993, WO-A-95/20660.

Likewise, D. TANG et al., (Nature 356, 152–154, Mar. 12, 1992) have shown the absence of immune response after the administration of human growth hormone by the intradermal route with the aid of a hypodermic needle. The authors have, on the other hand, demonstrated the obtaining of an immune response with the aid of the "gene gun" technique.

Only E. RAZ et al., (P.N.A.S. USA, Vol. 91, 9519–9523, September 1994) have reported that intradermal administration could induce high antibody titres.

For its part, the "gene gun" technique has the disadvantage of being difficult and expensive to use, since it requires the preparation and the use of gold particles coated with DNA and their administration with the aid of a special propellant.

Some authors have therefore developed an alternative technique which envisages the use of an apparatus for liquid jet administration. There may be mentioned P.A. FURTH et al. in Analytical Biochemistry 205, 365–368, 1992, who describe the use of the apparatus called Ped-o-jet, which is an injector used to deliver human vaccines into muscle tissues, for the administration of a DNA vaccine. The authors report that the injector can cause DNA to pass through the skin and reach the muscles, the fatty tissue and the mammary tissue of live animals.

H. L. VAHLSING et al., in Journal of Immunolog Methods 75 (1994) 11–22, describe the use of the apparatus called Med-E-Jet for transcutaneous and intramuscular administration.

There may also be mentioned M. JENKINS et al., in Vaccine 1995, Volume 13, No. 17, 1658–1664, who describe the use of jet vaccination into the muscle.

The bovine respiratory syncytial virus BRSV is present worldwide and can cause severe diseases of the lower respiratory tract in bovines, this disease being similar to that caused by the respiratory syncytial virus HRSV-in children. During one study, it was found that more than 95% of 2-year old calves were infected with the BRSV virus (Van der Poel et al., Archives of Virology 1993, 133, 309–321).

The need for a vaccine against the BRSV virus is felt but has not given rise to the development of effective vaccines. The first attempts to vaccinate children have led to the appearance of facilitation of the disease after natural infection, suggesting that the vaccination could be dangerous (Anderson et al., Journal of Infectious Diseases, 1995, 171: 1 to 7). It is known, however, that antibodies against the two major surface glycoproteins, F (fusion protein) and G (attachment protein) could play a role in protection (Kimman and Westenbrink, Archives of Virology, 1990, 112: to 25). Numerous studies have also been carried out on mouse-, dog- and ferret-type animal models. On the other hand, vaccination trials on bovines with the purified F protein have not given a conclusive result since, as in children vaccinated with HRSV, the calves developed neutralizing antibodies and nonneutralizing antibodies which could interfere with the immune response during a subsequent infection with the virus (L. D. Nelson et al., Am. J. Vet. Res., Vol. 53, No. 8, August 1992, p. 1315–1321).

The objective of the present invention is to provide an improvement in the vaccination of bovines with DNA, which makes it possible to ensure a vaccination which is at least as effective as vaccination by the intramuscular route or by the "gene gun" technique but which is easier and less expensive to use.

Another objective of the invention is to provide such an improvement leading to increased safety, essentially as regards the vaccination residues present in the tissues.

Another objective of the invention, which relates to the vaccination of animals intended for consumption, is also to ensure safety such that the vaccination has no unfavourable effect on the appearance of the meat.

Another objective of the invention is to provide a means for mass vaccination.

A specific objective of the invention is to provide such a vaccine allowing the protection of bovines against the BRSV virus, the IBR virus, the BVD virus or the PI-3 virus.

The Applicants have found that it is possible to meet these objectives by administering the vaccine by the intradermal route with the aid of a liquid injector without a needle, ensuring, at 5 points, distribution of the vaccine essentially in the epidermis, the dermis and the hypodermis. The trials conducted by the Applicants in the field of vaccination of bovines against the bovine respiratory syncytial virus (Bovine Respiratory Syncytial Virus, BRSV) have made it possible to obtain superior immunization results by this route compared to that obtained by the intramuscular route.

The present invention proposes, for the first time, the vaccination of bovines with polynucleotide vaccines (or DNA vaccines or plasmid vaccines) designed for, and administered by, the intradermal route by means of a liquid jet injector without a needle.

The subject of the present invention is therefore a polynucleotide vaccine formula comprising an intradermally effective quantity of a plasmid combining a DNA sequence encoding an immunogen and a promoter allowing the expression of this immunogen in vivo in the cells of the skin, this vaccine formula being suitable for intradermal administration (the cells of the epidermis, dermis and hypodermis are targeted in particular; the administration is intended in particular to present the expressed antigens to the dendritic Langerhans' cells of the skin, which cells are localized essentially in the epidermis) with an apparatus for liquid jet intradermal administration, in particular the apparatus called Pigjet (manufactured and distributed by Endoscoptic, Laons, France) or an equivalent apparatus delivering the vaccine through a 5-nozzle head under conditions equivalent to the Pigjet. In general, the vaccine formulae according to the invention are suitable for administration with an apparatus for liquid jet administration having from 1 to 10 nozzles, preferably from 4 to 6, still more preferably from 5 to 6.

This requires a vehicle suited to the intradermal route, such as water, buffer, physiological saline, liposomes, cationic lipids and, in general, a vehicle of low viscosity, especially equivalent or close to that of water, and a dose volume which is useful and effective by this route.

In particular, but not exclusively, with an apparatus having 5 or 6 nozzles, that is to say administering the dose through 5 or 6 openings and in the form of 5 or 6 jets of identical volume, the dose volume may be advantageously between 0.1 ml and 0.9 ml, preferably between 0.2 ml and 0.6 ml, preferably of the order of 0.4 to 0.5 ml.

The vaccine formula will comprise an intradermally effective quantity of plasmid which will be in general from 10 ng to 1 mg, preferably from 100 ng to 500 $\mu$g, preferably from 0.5 $\mu$g to 50 $\mu$g of plasmid.

Typically, the invention seeks to administer the vaccine formula at several points so as to optimize the transfection of cells with the plasmids. This results in a preference for the use of an injection head with several holes. This can also be combined with a multi-application of the apparatus, that is to say with the distribution of the vaccinal dose in more than one application of the apparatus at different sites. In a particularly preferred manner, it will be possible to use an apparatus with 5 or 6 holes in mono-application or in multi-application, preferably in double-application.

A typical case of the invention is a DNA sequence coding for an immunogen of the BRSV virus, and in particular for the G and/or F gene from this virus (for example 391-2 strain: R. Lerch et al., Virology, 1991, 181, 118–131).

Another typical case of the invention is a DNA sequence coding for an immunogen of the infectious bovine rhinotracheitis (IBR) virus or bovine herpes-virus (BHV), in particular for the gB gene and/or the gD gene (for example ST strain: Leung-Tack P. et al., Virology, 1994, 199, 409–421).

Another typical case of the invention is a DNA sequence encoding an immunogen of the mucosal disease virus bouine viral diarhea virus (BVD) in particular the E2 gene and/or the E1 gene (for example Osloss strain: L. De Moerlooze et al., J. Gen. Virol., 1993, 74, 1433–1438). It is also possible to combine genes from different subtypes of BVD, for example from North America and from Europe (A. Dekker at al., Veterinary Microbiol., 1995, 47, 317–329).

Yet another typical case of the invention is a DNA sequence coding for an immunogen of the type 3 parainfluenza virus (PI-3), in particular for the HN gene and/or the F gene, preferably the HN gene (sequence of the F and HN genes which was deposited by H. Shibuta in 1987, GeneBank sequence accession No. =Y00115).

In case of a combination of 2 genes, for example F and G from BRSV, HN and F from PI-3 or gD and gB from IBR, the corresponding sequences can be inserted into the same plasmid or into different plasmids.

Pathogenic agent gene is understood to mean not only the complete gene but also the various nucleotide sequences, including fragments, which retain the capacity to induce a protective response. The notion of a gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but which encode the same protein.

It is of course understood that the invention consists in the adaptation of the prior art DNA vaccines to an intradermal administration by an apparatus for liquid jet administration. While this results in modifications in the vaccine formula and in particular in the viscosity, the quantity of DNA and the dose volume to be administered, it goes without saying that the invention applies, moreover, to any DNA vaccine constructs described in the prior art. Persons skilled in the art will therefore be able to refer to the state of the art in the DNA vaccination field and in particular to the documents discussed above.

More specifically, the transcription units used in the vaccine formulae according to the invention will comprise a strong eukaryotic promoter, such as the hCMV IE promoter.

The vaccine formula according to the invention may be packaged in a multidose vial, for example of 10 to 100 doses, fitted to an apparatus for liquid jet intradermal administration, preferably the Pigjet.

The subject of the present invention is also a portable bovine vaccination unit comprising an apparatus for liquid jet administration and a suitable vial comprising several doses of a vaccine formula as described above, the apparatus for administration being designed so as to deliver a dose of vaccine formula intradermally.

Preferably, the apparatus for administration comprises an injection head provided with 1 to 10 nozzles, in particular from 4 to 6, preferably 5 or 6.

The apparatus for administration may have the different characteristics given in the detailed description. The preferred types of apparatus for administration are those which reproduce the administration conditions obtained with the Pigjet apparatus.

The subject of the present invention is also the use of a plasmid combining a DNA sequence encoding an immunogen of a bovine pathogen and a promoter allowing the expression of this type of immunogen, for the preparation of a polynucleotide vaccine formula according to the different procedures described above, suitable for intradermal administration with an apparatus for liquid jet administration.

The subject of the invention is also a method of vaccination in which a polynucleotide vaccine formula, as described above, is administered by the intradermal route with the aid of an apparatus for liquid jet administration. The administration of the vaccine may be done by one or more deliveries of a determined volume of formula. Likewise, it is possible to envisage one or more vaccinations distributed over time.

The method of vaccination according to the invention may take into account the data mentioned above as regards in particular the apparatus for administration to be used.

The invention will now be described in greater detail with the aid of the nonlimiting embodiments of the invention with reference to the accompanying drawings in which:

FIG. 1 describes a plasmid comprising the BRSV virus G gene under the control of the hCMV promoter, for the vaccination of bovines against this virus.

Figure 2:
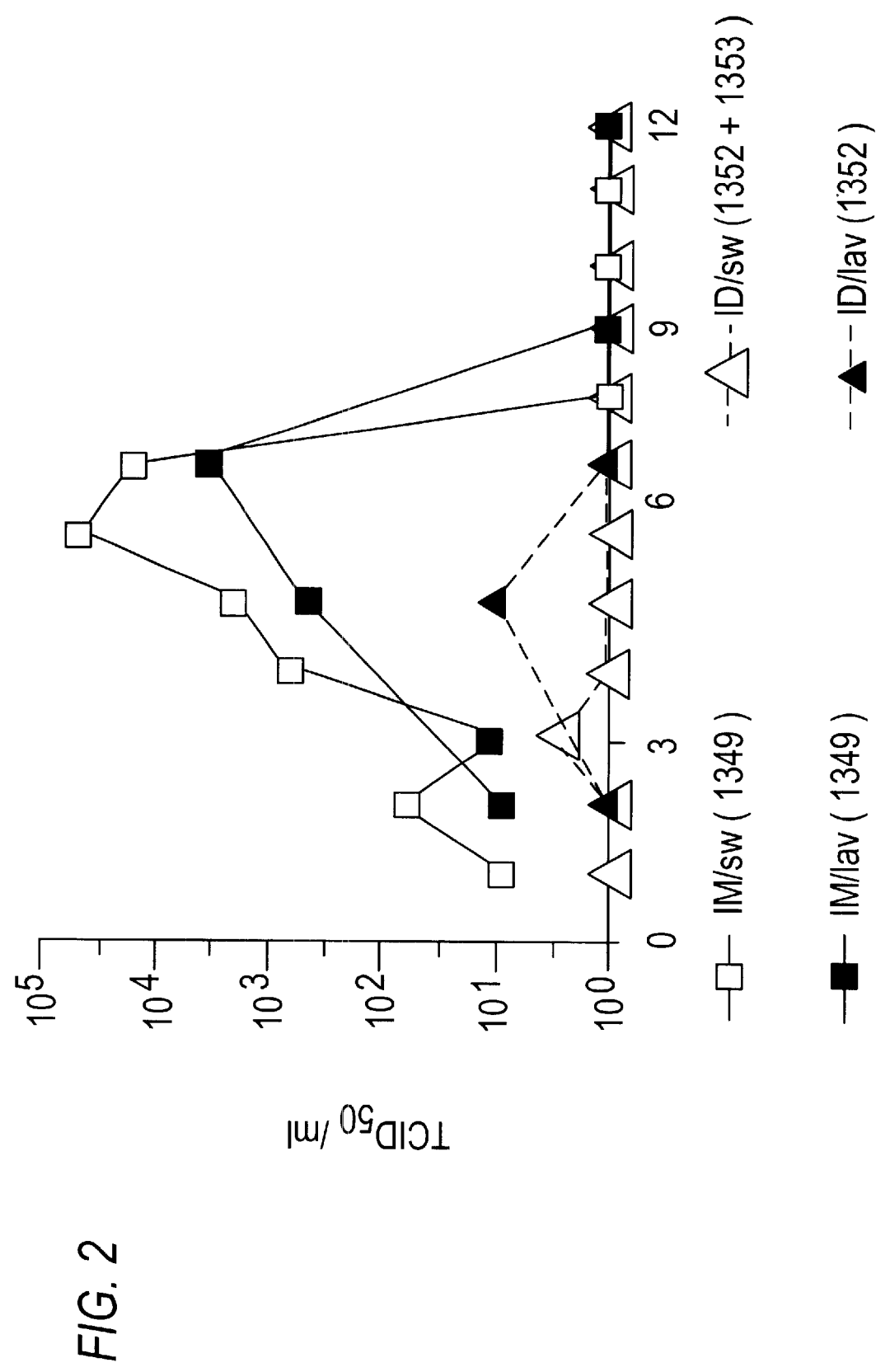

FIG. 2 represents a graph comparing the efficacy of the vaccination against the BRSV virus by the intramuscular IM route (bovine 1349) and the intradermal ID route (bovines 1352 and 1353), with the days on the x-axis and the infectious titre on the y-axis.

PREPARATION OF THE BRSV SYNTHETIC G GENE

The bovine respiratory syncytial virus is a Pneumovirus of the Paramyxovirus family. It is an enveloped virus which replicates in the cytoplasm and has a single-stranded genomic RNA in negative orientation. The BRSV genome encodes two major transmembrane glycoproteins, the fusion protein F and the attachment protein G.

A synthetic conversion of the G gene has been prepared by removing from this gene or the potential splicing signals (G. Keil, Federal Research Centre for Virus Diseases of Animals, Friedrich Löffler Institute, D-17498, Insel Riems, Germany).

The region encoding the G gene has been determined by Lerch et al., (Journal of Virology, 1990, 64, 5559–5569). The coding region corresponds to 257 amino acids and to the characteristic of a type II transmembrane glycoprotein. It has an N-terminal cytoplasmic domain of 40 amino acids followed by a transmembrane domain of 25 amino acids. The remainder, namely the 192 C-terminal amino acids, form the extracellular domain of the G protein. A DNA sequence has been synthesized having an open reading frame encoding exactly the same 257 amino acids found by Lerch et al., but without the potential splicing signals. The reverse translation of the sequence of 257 amino acids into all the possible DNA sequences encoding such an amino acid sequence has been carried out. This was carried out using the programme for reverse translation of a protein sequence RTRANS of PCGene by A. Bairoch., University of Geneva, Switzerland (IntelliGenetics Inc.). The potential splicing sites were determined using the "Signal" nucleic acid analysis programme. This programme is based on the Staden weighted matrix method (1984, Nucleic Acids Research 12, 505–519). This programme identifies the potential donor splicing sites (intron/exon borders) and the potential acceptor splicing sites (exon/intron borders). With the aid of these sequence data, it has been possible to mutate all the potential strong splicing signals without modifying the capacity for the protein. In particular, the GT dinucleotides which can form the 5' end of an intron and the AG dinucleotides which can form the 3' end of an intron were removed when possible.

To synthesize the suitable nucleotide sequence encoding G, oligonucleotides of about 100 residues covering the two strands of the complete sequence were synthesized with the aid of a DNA synthesizer (for example a Perkin Elmer/Applied Biosystems 381A DNA synthesizer; it is also possible to use commercially available oligonucleotides). The complementary oligonucleotides are hybridized so as to form a double-stranded fragment and cloned into prokaryotic vectors such as pUC18 or PUC19. Using appropriate enzymatic restriction sites, the cloned DNA fragments are linked together in the correct order using standard cloning procedures (Sambrook et al., Molecular Cloning: A laboratory Manual, 2nd edition, Cold Spring Harbor Laboratory, Cold Spring Harbor, N.Y. 1989). The nucleotide sequence of the DNA fragment which results therefrom was determined with the aid of standard sequencing procedures (Sambrook et al.) to check that the sequence is correct.

Construction of the eukaryotic expression vector comprising the G gene behind the hCKV promoter.

To ensure its expression, the synthetic G gene was cloned into a vector. In this preliminary trial, a vector immediately available in the laboratory, namely the eukaryotic expression vector 175hCMV, was used. This plasmid vector contains two fragments derived from the BHV1 virus which flanked at the origin the E gly-coprotein from the Dutch BHV1 strain called Lam (Van Engelenburg et al., 1994, Journal of General Virology 75, 2311–2318). The left-hand flanking fragment (Cterm gI) starts at the PstI site situated in the open reading frame of the gI glycoprotein and ends at the BstBi (or AsuII) site, 17 nucleotides upstream of the start of the open reading frame of the gE gene. This fragment is indicated by: Cterm gI. The right-hand flanking fragment starts at the EcoNI site situated at the level of the stop codon of the gE open reading frame and ends at the level of the first SmaI site upstream in the terminal repeat (Tr) fragment. This fragment encodes the US9 gene. This fragment is indicated by: US9 and TR. These two fragments were cloned into the PstI site and the EcoRI site (blunt end) of pUC18. Between the BstBI site and the EcoNI site, an AseI fragment (blunt end) of 720 bp containing the largest part of the human cytomegalovirus Immediate Early promoter (hCMV-P) was cloned with a polylinker region and ending with a polyadenylation signal (Poly A). The synthetic G gene was cloned in the orientation indicated inside the SmaI site of this polylinker region. The plasmid obtained was called PR608. See FIG. 1.

Control of the in vitro expression of G from the plasmid PR608:

A transient expression trial was carried out in order to test whether the plasmid PR608 can express the G protein. For this trial, 1.5 µg of purified DNA from the plasmid PR608 was transfected into a monolayer of embryonic bovine tracheal cells (EBTr) in culture. These EBTr cells were cultured in Eagle's minimum essential medium with l0%o foetal bovine serum (Integro) and antibiotics [125 IU of penicillin (Gist-Brocades), 125 µg of streptomycin (Biochemie), 37.5 IU of nystatin (Sigma) and 37.5 µg of kanamycin (Sigma) per ml]. The transfection was carried out in accordance with the standard calcium phosphate precipitation method according to F. L. Graham and A. J. van der Eb (1973, Virology 52, 456–467). After transfection, the plasmid DNA is transported into the nucleus of the transfected cells and the encoded proteins are expressed using the mechanism of the host cell. Normally, only 0.01% to 0.1% of the cells of the transfected monolayer will internalize the DNA and express the encoded genes.

Preparation of the DNA for the polynucleotide vaccination:

The DNA of the plasmid PR608 was prepared by adding 100 µl of a stock of *E. coli* K12 in glycerol, DH5alpha F- cells comprising the plasmid PR608, to 2 litres of LB medium, which is a standard medium for growing bacteria. This 2 litre culture is incubated at 37° C for 20 hours and the amplified cells are harvested using 250-ml flasks and an IEC Centra-8R centrifuge at maximum speed. The DNA of the plasmid PR608 was isolated from the cells of the pellet following the standard alkaline lysis method of Birnboim and Doly as described by Sambrook et al., (1989, Molecular Cloning, a Press Laboratory Manual, 2nd Ed., Cold Spring Harbor Laboratory Press). The plasmid DNA isolated was then dissolved in 20 ml of TE (10 mM Tris and 1 mM EDTA, pH 7.4) and subjected to electrophoresis to determine the DNA concentration and to assess the quality of DNA. From a normal 2 litre culture, it is possible to isolate 40 mg of plasmid; about 60i of the plasmid PR608 is found in the supercoiled state and about 30% in the relaxed circular state.

The plasmid preparation is stored at −20° C. Before application of the PR608 plasmid DNA, the DNA solution is diluted to 0.5 mg/ml in 1×PBS and TE. This buffered DNA solution is pipetted into 10-ml flasks fitted to the Pigjet apparatus and stored at 4° C. for use within 1 to 2 hours.

Piget apparatus for administration

The Pigjet-type, portable-type apparatus for administration comprises a casing provided with a handle, a chamber calibrated to 0.2 ml and a piston normally kept in the in position in the chamber by a spring integrally attached to the said piston.

The apparatus comprises, in addition, a head with 5 nozzles, intended to calibrate the jet, that is to say one head with 1 nozzle and a filtration device to avoid the injection of any possible impurities. The nozzles are slightly separated from each other.

The pressure of the jet at the outlet of the nozzle may be set at 100 bars for the Pigjet with 1 nozzle.

Brought about by appropriate means, the compression of the spring causes the movement of the piston and therefore the aspiration of the vaccine dose from a suitable reservoir or vial, attached to the casing.

Releasing the spring causes the return of the piston and the discharge of the dose through the nozzle(s).

Vaccination and challenge trials:

4 calves free of specific pathogenic organisms were obtained by Caesarean, were deprived of colostrum and were raised in isolation. The calves were vaccinated 6 times at 1-week intervals, from the age of 6 weeks. 2 animals -were vaccinated by the intradermal route by means of the Pigjet with 1 nozzle (Endoscoptic, Laons, France) and 2 animals were vaccinated by the intramuscular route with a 25-gauge needle. The Pigjet is applied so that its head is in contact with the skin and perpendicular thereto, in order that the jet of vaccine has a direction orthogonal to the skin. Each vaccination consisted of 500 µg of plasmid DNA in 1 ml of PBS phosphate buffer. The intradermal vaccination consisted of 5 injections of 0.2 ml into the skin of the hind leg and the intramuscular vaccinations consisted of 1 injection into the gluteus muscle. The skin was shaved before vaccination.

The antibody titres which appear in the following Table I were obtained:

vaccination at weeks 0, 1, 2, 3, 4, 5
challenge at week 6
monitoring of the antibody titre at weeks 0 to 8

|  | 0 | 1 | 2 | 3 | 4 | 5 | 6 | 7 | 8 |
|---|---|---|---|---|---|---|---|---|---|
| Calf 1352 Pigjet | <5 | <5 | <5 | 80 | 640 | 1280 | 640 | 1280 | >5120 |
| Calf 1453 Pigjet | <5 | <5 | <5 | 40 | 1280 | 640 | 640 | 640 | a |
| Calf 1349 IM | <5 | <5 | <5 | <5 | <5 | <5 | <5 | <5 | <5 |
| Calf 1350 IM | <5 | <5 | <5 | a | | | | | |

[a]These calves were sacrificed because of the appearance of major health problems unassociated with the vaccinations.

Following the DNA injections, the appearance of antibodies is observed at the end of 3 weeks in the animals vaccinated by the ID route and the appearance of high titres is observed from week 4, becoming a plateau.

The calves were then challenged with the infectious BRSV virus. The inoculation of the virus was carried out 6 weeks after the first vaccination by intranasal instillation of 1 ml of Odijk virus strain ($10^{3.8}$ $TCID_{50}$/ml) into each nostril.

To estimate the efficacy of the vaccination, the excretion of virus was monitored by the infectious titre $TCID_{50}$/ml up to 12 days after the infection, on nasopharyngeal swabs (sw) and in the lung washings fluid (Lav) (FIG. 2).

It was possible to demonstrate that a plasmid encoding the BRSV G protein administered by the intradermal route by liquid jet protected against a virulent challenge with this virus. The intradermal vaccination by means of an apparatus for administration having a discharge head with 1 hole rapidly induces high antibody titres against the G protein, which was not observed with the intramuscular vaccination. In addition, the infectious BRSV virus titres in the lung washing fluids and in the nasopharynigeal swabs were high in the calves vaccinated by the initramuscular route and virtually absent in the calves vaccinated by the intradermal route. The clinical signs were weak and were not markedly different between the animals.

A very good safety was also observed when the Pigjet was used, this technique not in fact-requiring a preliminary inflammation of the tissue to be induced as is the case with the gold particles.

In addition, what is remarkable is the obtaining of protection with the G protein which is ordinarily not very immunogenic (P. L. Collins in: The Paramyxoviruses, 1991, Ed. D. W. Kingsbury, N.Y., Plenum Press) and the high antibody titre obtained after intradermal vaccination is comparable with that obtained after natural infection or vaccination with a live vaccine tested in addition.

The invention also relates to the method for preparing the vaccine formulae, as given in this description.

What is claimed is:

1. A method for vaccinating a bovine against bovine respiratory syncytial virus (BRSV) comprising administering into the epidermis, dermis, or hypodermis of the bovine a vaccine that comprises a plasmid that contains and expresses in vivo in a bovine host skin cell a nucleic acid molecule having a sequence encoding the BRSV G protein operatively linked to a cytomegalovirus (CMV) IE promoter, by a liquid jet intradermal administration apparatus that administers the vaccine to the bovine without a needle into the epidermis, dermis, or hypodermis;

wherein the administration of said vaccine results in the generation of an immunological response in said bovine.

2. A vaccine against bovine respiratory syncytial virus (BRSV) comprising a plasmid that contains and expresses in vivo in a bovine host skin cell a nucleic acid molecule having a sequence encoding the BRSV G protein operatively linked to a cytomegalovirus (CMV) IE promoter, wherein the vaccine is in a liquid jet intradermal administration apparatus that administers the vaccine to the bovine: without a needle; and into the epidermis, dermis and/or hypodermis.

3. A liquid jet intradermal administration apparatus that administers a composition to an animal: without a needle, and into the epidermis, dermis and/or hypodermis; wherein the apparatus includes a vaccine against bovine respiratory syncytial virus (BRSV) comprising a plasmid that contains and expresses in vivo in a bovine host skin cell a nucleic acid molecule having a sequence encoding the BRSV G protein operatively linked to a cytomegalovirus (CMV) IE promoter.

4. The method of claim 1 wherein the bovine is a cow that is naïveas to BRSV.

5. The apparatus of claim 3 wherein the apparatus administers the composition at 1–10 points on the animal.

6. The apparatus of claim 3 wherein the apparatus administers the composition at 4–6 points on the animal.

7. The apparatus of claim 3 wherein the apparatus administers the composition at 5 or 6 points on the animal.

8. The apparatus of claim 3 wherein the apparatus administers the composition at 5 points on the animal.

9. The method of claim 1 wherein the apparatus administers the composition at 1–10 points on the bovine.

10. The method of claim 1 wherein the apparatus administers the composition at 4–6 points on the bovine.

11. The method of claim 1 wherein the apparatus administers the composition at 5 or 6 points on the bovine.

12. The method of claim 1 wherein the apparatus administers the composition at 5 points on the bovine.

13. The vaccine of claim 2 wherein the apparatus administers the composition at 1–10 points on the bovine.

14. The vaccine of claim 2 wherein the apparatus administers the composition at 4–6 points on the bovine.

15. The vaccine of claim 2 wherein the apparatus administers the composition at 5 or 6 points on the bovine.

16. The vaccine of claim 2 wherein the apparatus administers the composition at 5 points on the bovine.

17. A method for inducing an immunological response in a bovine against bovine respiratory syncytial virus (BRSV) comprising administering into the epidermis, dermis, or hypodermis of the bovine an immunological composition that comprises a plasmid that contains and expresses in vivo in a bovine host skin cell a nucleic acid molecule having a sequence encoding the BRSV G protein operatively linked to a cytomegalovirus (CMV) IE promoter, by a liquid jet intradermal administration apparatus that administers the composition to the bovine without a needle into the epidermis, dermis, or hypodermis; wherein the administration of said vaccine results in the generation of an immunological response in said bovine.

18. An immunogenic composition for inducing in a bovine host an immunological response against bovine respiratory syncytial virus (BRSV) comprising a plasmid that contains and expresses in vivo in a bovine host skin cell a nucleic acid molecule having a sequence encoding the BRSV G protein operatively linked to a cytomegalovirus (CMV) IE promoter, wherein the an immunological composition is in a liquid jet intradermal administration apparatus that administers the composition to the bovine: without a needle; and into the epidermis, dermis and/or hypodermis.

19. A liquid jet intradermal administration apparatus that administers a composition to an animal: without a needle, and into the epidermis, dermis and/or hypodermis; wherein the apparatus includes an immunogenic composition for inducing in a bovine host an immunological response against bovine respiratory syncytial virus (BRSV) comprising a plasmid that contains and expresses in vivo in a bovine host skin cell a nucleic acid molecule having a sequence encoding the BRSV G protein operatively linked to a cytomegalovirus (CMV) IE promoter.

20. The method of claim 17 wherein the bovine is a cow that is naïveas to BRSV.

21. The apparatus of claim 19 wherein the apparatus administers the composition at 1–10 points on the animal.

22. The apparatus of claim 19 wherein the apparatus administers the composition at 4–6 points on the animal.

23. The apparatus of claim 19 wherein the apparatus administers the composition at 5 or 6 points on the animal.

24. The apparatus of claim 19 wherein the apparatus administers the composition at 5 points on the animal.

25. The method of claim 17 wherein the apparatus administers the composition at 1–10 points on the bovine.

26. The method of claim 17 wherein the apparatus administers the composition at 4–6 points on the bovine.

27. The method of claim 17 wherein the apparatus administers the composition at 5 or 6 points on the bovine.

28. The method of claim 17 wherein the apparatus administers the composition at 5 points on the bovine.

29. The immunogenic composition of claim 18 wherein the apparatus administers the composition at 1–10 points on the bovine.

30. The immunogenic composition of claim 18 wherein the apparatus administers the composition at 4–6 points on the bovine.

31. The immunogenic composition of claim 18 wherein the apparatus administers the composition at 5 or 6 points on the bovine.

32. The immunogenic composition of claim 18 wherein the apparatus administers the composition at 5 points on the bovine.

33. A method for vaccinating a bovine against infectious bovine rhinotracheitis virus (IBR virus) comprising administering into the epidermis, dermis, or hypodermis of the bovine a vaccine that comprises a plasmid that contains and expresses in vivo in a bovine host skin cell a nucleic acid molecule having a sequence encoding the IBR virus gB protein operatively linked to a cytomegalovirus (CMV) IE promoter, by a liquid jet intradermal administration apparatus that administers the vaccine to the bovine without a needle into the epidermis, dermis, or hypodermis; wherein the administration of said vaccine results in the generation of an immunological response in said bovine.

34. A vaccine against infectious bovine rhinotracheitis virus (IBR virus) comprising a plasmid that contains and expresses in vivo in a bovine host skin cell a nucleic acid molecule having a sequence encoding the IBR virus gB protein operatively linked to a cytomegalovirus (CMV) IE promoter, wherein the vaccine is in a liquid jet intradermal administration apparatus that administers the vaccine to the bovine: without a needle; and into the epidermis, dermis and/or hypodermis.

35. A liquid jet intradermal administration apparatus that administers a composition to an animal: without a needle, and into the epidermis, dermis and/or hypodermis; wherein the apparatus includes a vaccine against infectious bovine rhinotracheitis virus (IBR virus) comprising a plasmid that contains and expresses in vivo in a bovine host skin cell a nucleic acid molecule having a sequence encoding the IBR virus gB protein operatively linked to a cytomegalovirus (CMV) IE promoter.

36. The method of claim 32 wherein the bovine is a cow that is naïveas to the IBR virus.

37. The apparatus of claim 35 wherein the apparatus administers the composition at 1–10 points on the animal.

38. The apparatus of claim 35 wherein the apparatus administers the composition at 4–6 points on the animal.

39. The apparatus of claim 35 wherein the apparatus administers the composition at 5 or 6 points on the animal.

40. The apparatus of claim 35 wherein the apparatus administers the composition at 5 points on the animal.

41. The method of claim 33 wherein the apparatus administers the composition at 1–10 points on the bovine.

42. The method of claim 33 wherein the apparatus administers the composition at 4–6 points on the bovine.

43. The method of claim 33 wherein the apparatus administers the composition at 5 or 6 points on the bovine.

44. The method of claim 33 wherein the apparatus administers the composition at 5 points on the bovine.

45. The vaccine of claim 34 wherein the apparatus administers the composition at 1–10 points on the bovine.

46. The vaccine of claim 34 wherein the apparatus administers the composition at 4–6 points on the bovine.

47. The vaccine of claim 34 wherein the apparatus administers the composition at 5 or 6 points on the bovine.

48. The vaccine of claim 34 wherein the apparatus administers the composition at 5 points on the bovine.

49. A method for inducing an immunological response in a bovine against infectious bovine rhinotracheitis virus (IBR virus) comprising administering into the epidermis, dermis, or hypodermis of the bovine an immunological composition that comprises a plasmid that contains and expresses in vivo in a bovine host skin cell a nucleic acid molecule having a sequence encoding the IBR virus gB protein operatively linked to a cytomegalovirus (CMV) IE promoter, by a liquid jet intradermal administration apparatus that administers the composition to the bovine without a needle into the epidermis, dermis, or hypodermis; wherein the administration of said vaccine results in the generation of an immunological response in said bovine.

50. An immunogenic composition for inducing in a bovine host an immunological response against bovine infectious bovine rhinotracheitis virus (IBR virus) comprising a plasmid that contains and expresses in vivo in a bovine host skin cell a nucleic acid molecule having a sequence encoding the IBR virus gB protein operatively linked to a cytomegalovirus (CMV) IE promoter, wherein the immunogenic composition is in a liquid jet intradermal administration apparatus that administers the immunogenic composition to the bovine: without a needle; and into the epidermis, dermis and/or hypodermis.

51. A liquid jet intradermal administration apparatus that administers a composition to an animal: without a needle, and into the epidermis, dermis and/or hypodermis; wherein the apparatus includes an immunogenic composition for inducing in a bovine host an immunological response against infectious bovine rhinotracheitis virus (IBR virus) comprising a plasmid that contains and expresses in vivo in a bovine host skin cell a nucleic acid molecule having a sequence encoding the IBR virus gt protein operatively linked to a cytomegalovirus (CMV) IE promoter.

52. The method of claim 49 wherein the bovine is a cow that is naïveas to the IBR virus.

53. The apparatus of claim 51 wherein the apparatus administers the composition at 1–10 points on the animal.

54. The apparatus of claim 51 wherein the apparatus administers the composition at 4–6 points on the animal.

55. The apparatus of claim 51 wherein the apparatus administers the composition at 5 or 6 points on the animal.

56. The apparatus of claim 51 wherein the apparatus administers the composition at 5 points on the animal.

57. The method of claim 49 wherein the apparatus administers the composition at 1–10 points on the bovine.

58. The method of claim 49 wherein the apparatus administers the composition at 4–6 points on the bovine.

59. The method of claim 49 wherein the apparatus administers the composition at 5 or 6 points on the bovine.

60. The method of claim 49 wherein the apparatus administers the composition at 5 points on the bovine.

61. The immunogenic composition of claim 50 wherein the apparatus administers the composition at 1–10 points on the bovine.

62. The immunogenic composition of claim 50 wherein the apparatus administers the composition at 4–6 points on the bovine.

63. The immunogenic composition of claim 50 wherein the apparatus administers the composition at 5 or 6 points on the bovine.

64. The immunogenic composition of claim 50 wherein the apparatus administers the composition at 5 points on the bovine.

65. A method for vaccinating a bovine against bovine respiratory syncytial virus (BRSV) comprising administering into the epidermis, dermis, or hypodermis of the bovine a vaccine that comprises a plasmid that contains and expresses in vivo in a bovine host skin cell a nucleic acid molecule having a sequence encoding the BRSV F protein operatively linked to a cytomegalovirus (CMV) IE promoter, by a liquid jet intradermal administration apparatus that administers the vaccine to the bovine without a needle into the epidermis, dermis, or hypodermis; wherein the administration of said vaccine results in the generation of an immunological response in said bovine.

66. An immunogenic composition or vaccine against bovine respiratory syncytial virus (BRSV) comprising a plasmid that contains and expresses in vivo in a bovine host skin cell a nucleic acid molecule having a sequence encoding the BRSV F protein operatively linked to a cytomegalovirus (CMV) IE promoter, wherein the immunogenic composition or vaccine is in a liquid jet intradermal administration apparatus that administers the composition to the bovine: without a needle; and into the epidermis, dermis and/or hypodermis.

67. A liquid jet intradermal administration apparatus that administers an immunogenic composition or vaccine to an animal: without a needle, and into the epidermis, dermis and/or hypodermis; wherein the apparatus includes an immunogenic composition or vaccine for inducing in a bovine host an immunological response against bovine respiratory syncytial virus (BRSV) comprising a plasmid that contains and expresses in vivo in a bovine host skin cell a nucleic acid molecule having a sequence encoding the BRSV F protein operatively linked to a cytomegalovirus (CMV) IE promoter.

68. The method of claim 65 wherein the bovine is a cow that is naïveas to BRSV.

69. The apparatus of claim 67 wherein the apparatus administers the composition or vaccine at 1–10 points on the animal.

70. The apparatus of claim 67 wherein the apparatus administers the composition or vaccine at 4–6 points on the animal.

71. The apparatus of claim 67 wherein the apparatus administers the composition or vaccine at 5 or 6 points on the animal.

72. The apparatus of claim 67 wherein the apparatus administers the composition or vaccine at 5 points on the animal.

73. The method of claim 65 wherein the apparatus administers the composition or vaccine at 1–10 points on the bovine.

74. The method of claim 65 wherein the apparatus administers the composition or vaccine at 4–6 points on the bovine.

75. The method of claim 65 wherein the apparatus administers the composition or vaccine at 5 or 6 points on the bovine.

76. The method of claim 65 wherein the apparatus administers the c composition or vaccine at 5 points on the bovine.

77. The immunogenic composition or vaccine of claim 66 wherein the apparatus administers the composition or vaccine at 1–10 points on the bovine.

78. The immunogenic composition or vaccine of claim 66 wherein the apparatus administers the composition or vaccine at 4–6 points on the bovine.

79. The immunogenic composition or vaccine of claim 66 wherein the apparatus administers the composition or vaccine at 5 or 6 points on the bovine.

80. The immunogenic composition or vaccine of claim 66 wherein the apparatus administers the composition at 5 points on the bovine.

* * * * *

UNITED STATES PATENT AND TRADEMARK OFFICE
CERTIFICATE OF CORRECTION

PATENT NO.      : 6,451,770 B1
DATED           : September 17, 2002
INVENTOR(S)   : Franciscus Antonius Maria Rijsewijk et al.

It is certified that error appears in the above-identified patent and that said Letters Patent is hereby corrected as shown below:

Title page,
Item [54], change "BOVINE NUCLETIDE VACCINE FOR THE INTRADERMAL ROUTE" to -- BOVINE NUCLEOTIDE VACCINE FOR THE INTRADERMAL ROUTE --.
Item [73], Assignees: change "Lyons" to -- Lyon --.

Column 12,
Line 5, change "gt protein" to -- gB protein --.

Signed and Sealed this

Twenty-eighth Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,451,770 B1
DATED : September 17, 2002
INVENTOR(S) : Franciscus Antonius Maria Rijsewijk et al.

It is certified that error appears in the above-identified patent and that said Letters Patent is hereby corrected as shown below:

Title page,
Item [54], change "BOVINE POLYNUCLETIDE VACCINE FOR THE INTRADERMAL ROUTE" to -- BOVINE POLYNUCLEOTIDE VACCINE FOR THE INTRADERMAL ROUTE --.
Item [73], Assignees: change "Lyons" to -- Lyon --.

Column 12,
Line 5, change "gt protein" to -- gB protein --.

This certificate supersedes Certificate of Correction issued January 28, 2003.

Signed and Sealed this

Twenty-ninth Day of April, 2003

JAMES E. ROGAN
*Director of the United States Patent and Trademark Office*